United States Patent [19]

Wyss et al.

[11] Patent Number: 4,787,908
[45] Date of Patent: Nov. 29, 1988

[54] METATARSAL-PHALANGEAL REPLACEMENT JOINT

[75] Inventors: Urs Wyss, Inverary; Gerald A. B. Saunders, Sydenham; David Siu; Theodore D. Cooke, both of Kingston, all of Canada; Yuki Yoshioka, Kobe, Japan; J. Timothy Bryant, Kingston, Canada

[73] Assignee: Queen's University at Kingston, Kingston, Canada

[21] Appl. No.: 44,194

[22] Filed: Apr. 30, 1987

[51] Int. Cl.[4] .................................................. A61F 2/42
[52] U.S. Cl. ......................................... 623/21; 623/18
[58] Field of Search ................... 623/21, 16, 18, 66, 623/20

[56]  References Cited
U.S. PATENT DOCUMENTS

| 3,946,445 | 3/1976 | Bentley et al. | 623/21 X |
| 4,011,603 | 3/1977 | Steffee | 623/21 |
| 4,156,296 | 5/1979 | Johnson et al. | 623/21 |
| 4,213,208 | 7/1980 | Marne | 623/21 |
| 4,231,121 | 11/1980 | Lewis | 623/21 |
| 4,242,759 | 1/1981 | White | 623/21 |
| 4,385,404 | 5/1983 | Sully et al. | 623/21 K |
| 4,642,122 | 2/1987 | Steffee | 623/21 |

Primary Examiner—Richard J. Apley
Assistant Examiner—Alan W. Cannon
Attorney, Agent, or Firm—Richard J. Hicks

[57] ABSTRACT

An endoprosthetic metatarsal-phalangeal replacement joint is described. The joint includes a distal metatarsal component having a part-spherical convex distal superior phalangeal articular surface, and two inferior "side-by-side" sesamoidal articular surfaces, separated by an intersesamoidal ridge. The proximal phalangeal component is provided with a proximal circular surface at least a major portion of which has a part spherical concave surface having similar radius of curvature as the distal superior phalangeal surface of the metatarsal component. Natural, natural-resurfaced or prosthetic sesamoids are secured to a flexible mesh element arranged to be secured between the phalangeal component and the phalanx so that the sesamoids are positioned for articulation with the two inferior sesamoidal surfaces of the distal metatarsal component.

14 Claims, 2 Drawing Sheets

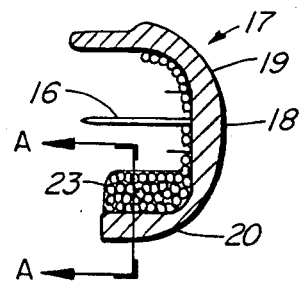
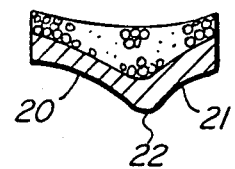
FIG. 5　　　　　FIG. 6
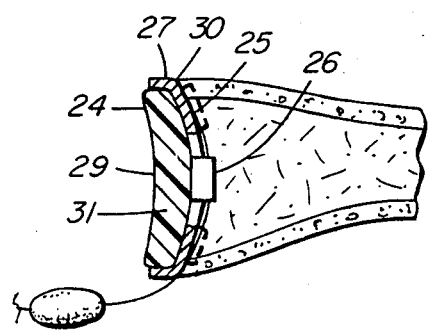
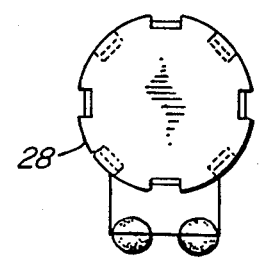
FIG. 7　　　　　FIG. 8
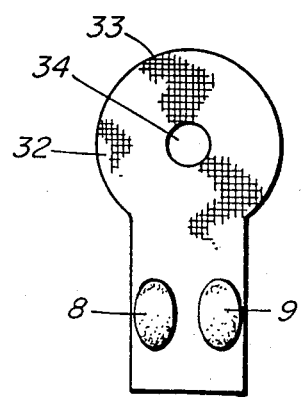
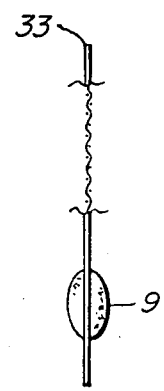
FIG. 9　　　　　FIG. 10

METATARSAL-PHALANGEAL REPLACEMENT JOINT

FIELD OF INVENTION

This invention relates to a prosthetic device for the replacement of joints in human beings. More particularly this invention relates to an endoprosthetic metatarso-phalangeal (great or big toe) joint for a human being.

DESCRIPTION OF THE PRIOR ART

Several prosthetic metatarso-phalangeal (MTP) joints have been described in the general and patent literature. For example, U.S. Pat. No. 4,213,208 describes a total joint replacement, constrained to act in three degrees of movement, which is secured in place by means of long stems which limit the ability of the device to transmit torsional loads. U.S. Pat. No. 4,156,296 describes an essentially unconstrained prosthesis for replacement of a joint in fingers and toes having a proximal component with a convex part spherical bearing surface and a distal component with a matching concave, part spherical bearing surface, the area of contact being such that the surfaces slide free relative to each other in a universal manner. This is a relatively simplistic approach and in no way replicates an actual metatarsal-phalangeal joint in that, in common with other prior art prostheses, it completely overlooks the fact that the articular surface of the metatarsal includes three entirely separate bearing surfaces and not merely the usually recognized part-spherical distal superior phalangeal surface. There are, in fact, two inferior "side-by-side" sesamoidal (tibial and fibular) surfaces, which play an important role during proper load bearing gait and which have, heretofore, been ignored by prosthetic device manufacturers.

SUMMARY OF INVENTION

It is an object of the present invention to provide an improved metatarsal-phalangeal joint resurfacing prosthesis which recognizes the importance of the sesamoids and which seeks to preserve them or to provide a prosthesis therefor.

Thus, by one aspect of this invention there is provided an endoprosthetic device for replacement, in a living body, of a first metatarsal phalangeal joint, comprising a metatarsal component having:
(i) a distal head with a smooth distal surface having a superior part-spherical convex phalangeal surface and two inferior, side-by-side concave sesamoidal surfaces, which are separated by an intersesamoidal ridge, blending smoothly with each other.

By another aspect there is provided an endoprosthetic device for replacement, in a living body, of a first metatarsal phalangeal joint, comprising:
(a) a biologically compatible-metallic metatarsal component having:
  (i) a distal head with a smooth distal surface having a superior part-spherical convex phalangeal surface and two inferior, side-by-side concave sesamoidal surfaces, which are separated by an intersesamoidal ridge, blending smoothly with each other;
(b) a phalangeal component having:
  (i) an axially extending distal stem for intramedullar implantation into a proximal phalanx; and
  (ii) a proximal head, integrally formed with said distal stem, having a smooth proximal circular surface at least a major portion of which is a biologically compatible polymeric material having a part spherical concave surface having a similar radius of curvature as said superior part-spherical convex phalangeal surface; and
(c) a sesamoidal component having:
  (i) an elongated flexible planar element including means for securing said element, adjacent a distal end thereof, to said proximal phalanx, and
  (ii) tibial and fibular sesamoidal elements mounted on said planar element in spaced lateral relationship to each other adjacent a proximal end thereof, for articulation with said inferior concave sesamoidal surfaces of said metatarsal component.

BRIEF DESCRIPTION OF DRAWINGS

The invention will be described in more detail hereinafter by reference to the accompanying drawings in which:

FIG. 5 is a side sectional view of the metatarsal prosthesis of the present invention;
FIG. 6 is a sectional view taken along A—A of FIG. 5;
FIG. 7 is a lateral sectional view of the phalangeal component of the present invention;
FIG. 8 is a proximal end view of the phalangeal component of FIG. 7.
FIG. 9 is a plan view of the sesamoidal component of the present invention;
and
FIG. 10 is a side view of the proximal end of the sesamoidal component of FIG. 9.

DESCRIPTION OF THE PREFERRED EMBODIMENT

Figure 1:
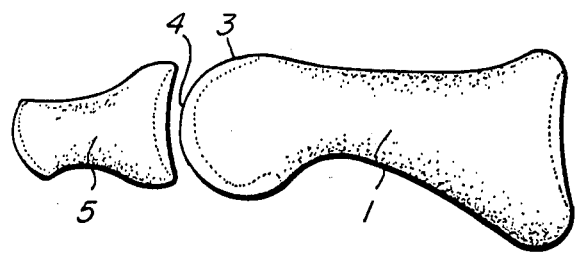
FIG. 1 is a lateral view of the MTP joint.
Figure 2:
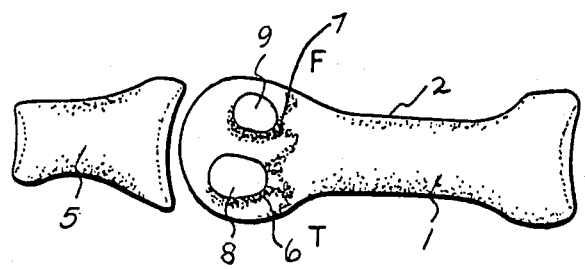
FIG. 2 is a planter view of the MTP joint.
Figure 3:
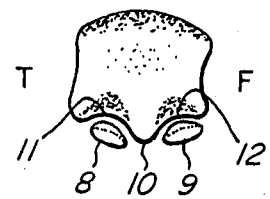
FIG. 3 is an axial view of the MTP joint.

The body of the first metatarsal 1 (FIGS. 1, 2 and 3), which is the shortest and thickest amongst the five metatarsals, has a well-marked prismatic form with three characteristic surfaces and borders: dorsomedial, lateral and inferior surfaces with superolateral, inferolateral and inferomedial borders. The lateral surface 2 is consistently flat and appears in line with the vertical orientation of the tarsometatarsal joint. Compared with lesser metatarsal heads, the first MT head 3 is larger and quadrilateral in general outline. The articular surface has three distinct bearing areas: a distal superior phalangeal surface 4 which articulates with phalanx 5 and two inferior "side-by-side" sesamoidal (tibial and fibular) surfaces 6 and 7 which articulate with sesamoids 8 and 9. These overlap and interrelate with each other closely such that separate borders for 'territorial' motion of each cannot be precisely identified. The phalangeal bearing area 4 of the head is smooth and convex. From the plantar aspect, a longitudinal crest, the intersesamoid ridge 10, rises between two grooves (trochlea) 11,12. The grooves articulate with dorsal biconcave articular surfaces of the tibial and fibular sesamoids 8 and 9 respectively and, in flexion, with the inferior portion of the proximal phalanx 5. In its proximal plantar extent, the ridge becomes less distinct but the grooves continue the side-by-side articular surfaces for the sesamoids proximally. Distally, the ridge and grooves merge with the rounded form of the head at a point in line with the bony axis of the bone. The outer (lateral) aspects of the MT head show bony protrusions (epicondyles) which have been reported as well developed bonyl tubercles from which the collateral ligaments arise.

The recorded range of motion of the first MTP has been reported as: 45 and 70 degrees of passive flexion/extension with 21 and 51 degrees of active flexion/extension. In stance, which may be considered to be a neutral position of the MTP, the joint lies at some 16 to 20 degrees of extension. This position is dependent upon the elevation of the medial longitudinal arch of the foot. Normal toe-off requires a minimum of 35 to 40 degrees of extension. There is a limited degree of abduction and adduction movement in the first MTP. Rotation, although likely to occur during push off from uneven surfaces, is not defined. The usual position of the phalanx is 15 degrees valgus to the first ray. Such is influenced by the degree of varus of the first ray, greater in the splayed forefoot than in the narrow foot.

There are three specific features of the first MTP joint not seen in any other joints. First, the extension motion range is of more importance than the flexion range; the joint is usually 'forced' to extend in stance, during walking and running. Second, it has a complex configuration which continues a multiaxial distal part with a saddle-shaped plantar part forming three closely related articulations; all influence joint function. Third, the maximal loads in stance and gait are exerted on the joint perpendicular to the long axis of the metatarsal head; loads apply directly between the MT trochlea and the tibial sesamoid.

It has now been found that the intersesamoid ridge, which is the most striking anatomic structure of the MT articular surface, is oriented parallel to the lateral surface of the metatarsal shaft and in line with the MT superolateral border. In other words, the plane of the ridge is sagittal with respect to the MT long axis but in turn rotated medially by 13 degrees in stance. A single geometric center has been found in the MT head in the area of the ridge. The contour of which is circular. The arcs of the articular outlines out of the plane of the intersesamoidal ridge are complex, representing the combined side-by-side articulations of the sesamoids. Geometric centers are not found for the MT head at any distance from the ridge.

Figure 4:
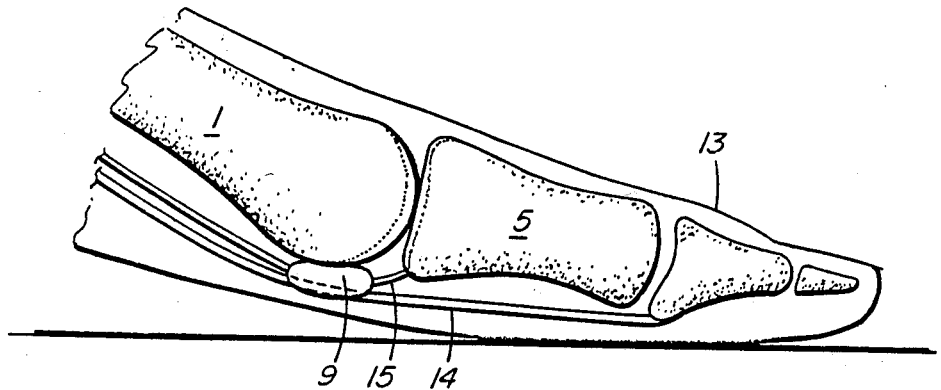
FIG. 4 is a sketch showing a lateral view in section of the great toe.

In the standing plantigrade positions (FIG. 4), about one third of body weight is borne by the forepart of the foot; this, carried through the head of the first metatarsal 1, equals about one sixth body weight. In walking, the center of gravity passes through the big toe 13 such that loads of more than the body weight occur via the plantar articulations. MTP joint organization may be compared to the condylar patella organization of the knee; here one is viewing the MTP in reverse and assuming the two sesamoids 8,9 to be patellae, with the phalangosesamoid apparatus and flexor hallucis longus tendons 14 to be the quadriceps mechanism. The motion of extension at the MTP corresponds more to the flexion of the knee. In extension, the convex MT head has greater contact with the elliptical concave facet of the phalanx 5; here the intersesamoid ridge does not interrupt this conformity as it occupies the slot made by the upward projections of the two sesamoids on either side of the thick plantar plate 15. The form of this articulation is akin to a rail and truck mechanism which provides side to side stability during flexion/extension motion of the phalanx. In extension beyond about zero degrees, the intersesamoid ridge merges with the convex outline of the phalangeal articular surface. In positions of MTP extension greater than approximately 10 degrees, the sesamoids come to lie on this same surface, now without sideways restraint (no ridge or groove). Beyond this point, the sesamoids may be passively subluxed to either side. In flexion, the phalangeal surface loses contact with the inferior part of the MTP head on either side of the ridge. Passive sideways angulation is readily achieved in this position. These observations may have relationships to valgus subluxation, deformities and/or arthritis.

Thus, the projection of the ridge and the angles formed by both trochlear surfaces of the heads as well as the congruity of the sesamometatarsal joint will directly influence sideways motion or angulation of the phalanx. Lack of the ridge (maldevelopment of disease), the phase of the MTP motion and/or torsional malalignment of the MT head, may each be contributing factors that may lead to lateral instabilitly of the sesamoids and subsequent MTP deformity. In this regard, the chronic use of high heeled shoes perpetuating hyperextension may chronically locate the sesamoids at a potentially unstable site, potentiating their lateral subluxation.

It will be appreciated by those skilled in the art, therefore, that the sesamoid bones and their guidance by the ridge and groove configuration of the metatarsal head are of considerable importance in any consideration of a truly functional MTP prosthesis. There are clearly clinical situations in which the generally accepted treatment—removal of the sesamoids completely—is not appropriate and an improved prosthesis which retains the sesamoids is desirable.

In a preferred embodiment of the present invention the prosthesis comprises a distal metatarsal component a proximal phalangeal component and, a sesamoidal component which may be secured to the phalangeal component or approached independently.

The distal metatarsal component is a unitary body, as shown in FIGS. 5 and 6, and comprises a short proximal axially extending stem 16 integrally connected to the proximal side of a distal head 17 which is provided with a smooth distal surface 18 having a superior part-spherical phalangeal surface 19, and two inferior, side-by-side concave sesamoidal surfaces 20, 21, separated by an intersesamoidal ridge 22, blending smoothly with each other. It will be appreciated that the axial stem 16 is a preferred but not an essential element of the metatarsal component. The proximal side of head 17 is a substantially concave hemispherical or truncated conical shape, preferably provided with an inferior flattened sided 23 which prevents axial rotation of the prosthesis as implanted. Alternative means to prevent rotation may, of course, also be incorporated, such as supplementary axis pins or ridges on the proximal surface. The concave proximal shape is selected, as required, depending on the type of cutting device used to prepare the bone and the clinical condition thereof. It is also contemplated that the concave proximal surface may be provided with a porous coating such as a plurality of spherical metal beads in known manner, so as to promote bone-ingrowth. The metatarsal component may be fabricated in any physiologically acceptable metal alloy such as a cobalt based alloy commonly known as Vitallium (Howmedia, U.S.A.), and is preferably fabricated from a titanium alloy such as Protasul-64WS (Sulzer Bros., Switzerland).

The proximal phalangeal component is also generally a unitary body and, as shown in FIGS. 7 and 8 comprises a proximal head 24 which is defined by a circular substantially flat distal surface 25, from which an axial distal stem 26 extends substantially perpendicularly therefrom, a proximal circular surface 28, at least a major part of which is formed as a part spherical concave smooth surface 29 having a similar radius of curvature as the part-spherical convex surface 19 of head 18 of the metatarsal component. Preferably the phalangeal component is fabricated from high density polyethylene (HDPE) or similar thermoplastics material. It may however be formed as a metallic, preferably titanium, "cup" 30 with an HDPE articulating surface insert 31 therein.

The sesamoidal component, as shown in FIGS. 9 and 10, comprises a flexible mesh element 32, preferably of titanium or polymeric material of either resorbing or non-resorbing type, arranged for attachment to the proximal phalanx. In the embodiment shown in FIG. 9, longitudinally extending strip 32 is provided with a substantially circular end 33 having a diameter approximating that of the distal phalangeal surface 25. A central hole 34 is provided in end 33 and adapted to receive axial distal stem 26 therethrough, so as to secure the sesamoidal component between the phalangeal component and the proximal prepared end of the phalanx. At the other end of strip 32, the fibular and tibial sesamoids 9 and 8 are secured in appropriate spaced relation. Sesamoids 8 and 9 may be the biological sesamoids secured to the mesh material by any convenient surgical means such as pinning or stapling, or the sesamoids may be prosthetic in nature, being fabricated in a high density plastic such as polyethylene or the natural sesamoids with either a metallic or plastic shell or coating cemented thereto, depending upon the clinical condition in any particular case. It will also be appreciated that if the natural ligature is intact the biological sesamoids may be retained therewith without reliance on the mesh element for attachment. Equally biological or resurfaced biological sesamoids may simply be secured together for natural retention.

We claim:

1. An endoprosthetic device for replacement, in a living body, of a first metatarsal phalangeal joint, comprising a metatarsal component having:
   (i) a distal head having a substantially concave proximal surface with a smooth distal surface having a superior part-spherical convex phalangeal surface and two inferior, side-by-side concave sesamoidal surfaces, which are separated by an intersesamoidal ridge, blending smoothly with each other,
   and including a phalangeal component having:
   (i) an axially extending distal stem for intramedullar implantation into a proximal phalanx; and
   (ii) a proximal head, integrally formed with said distal stem, having a smooth proximal circular surface at least a major portion of which has a part spherical concave surface having a similar radius of curvature as said superior part-spherical convex phalangeal surface.

2. An endoprosthetic device as claimed in claim 1 wherein said proximal head of said phalangeal component has a substantially concave distal surface from which said distal stem extends axially.

3. An endoprosthetic device as claimed in claim 1 wherein said distal head of said metatarsal component has a substantially concave proximal surface.

4. An endoprosthetic device as claimed in claim 1 wherein said proximal surface is substantially hemispherical.

5. An endoprosthetic device as claimed in claim 1 wherein said proximal surface is substantially truncated conical.

6. An endoprosthetic device as claimed in claim 3 wherein said metatarsal component includes an axially extending proximal stem for intramedullar implantation in to a distal metatarsal bone, integrally formed with and extending axially from said concave proximal surface thereof.

7. An endoprosthetic device as claimd in claim 2 wherein said sesamoidal elements are natural sesamoids.

8. An endoprosthetic device as claimed in claim 2 wherein said sesamoidal elements are prosthetic sesamoids.

9. An endoprosthetic device as claimed in claim 2 wherein said sesamoidal elements are prosthetically resurfaced natural sesamoids.

10. An endoprosthetic device as claimed in claim including sesamoidal elements arranged to articulate with said concave sesamoidal elements.

11. An endoprosthetic device as claimed in claim 1 including a sesamoidal component comprising:
   (i) An elongated flexible planar element including means for securing said element, adjacent a distal end thereof, to said proximal phalanx; and
   (ii) tibial and fibular sesamoidal elements mounted on said planar element in spaced lateral relationship to each other adjacent a proximal end thereof, for articulation with said inferior concave sesamoidal surfaces of said metatarsal component.

12. An endoprosthetic device for replacement, in a living body, of a first metatarsal phalangeal joint, comprising:
   (a) a biologically compatible-metallic metatarsal component having:
      (i) a distal head and with a smooth distal surface having a superior part-spherical convex phalangeal surface and two inferior, side-by-side concave sesamoidal surfaces, which are separated by an intersesamoidal ridge, blending smoothly with each other;
   (b) a phalangeal component having:
      (i) an axially extending distal stem for intramedullar implantation into a proximal phalanx; and
      (ii) a proximal head, integrally formed with said distal stem, having a smooth proximal circular surface at least a major portion of which is a biologically compatible plastics material having a part-spherical concave surface having a similar radius of curvature as said superior part-spherical convex phalangeal surface; and
   (c) a sesamoidal component having:
      (i) An elongated flexible planar element including means for securing said element, adjacent a distal end thereof, to said proximal phalanx, and
      (ii) tibial and fibular sesamoidal elements mounted on said planar element in spaced lateral relationship to each other adjacent a proximal end thereof, for articulation with said inferior concave sesamoidal surfaces of said metatarsal component.

13. An endoprosthetic device as claimed in claim 12 wherein said metatarsal component includes an axially extending proximal stem for intramedullar implantation into a distal metatarsal bone, integrally formed with and extending from said distal surface thereof.

14. An endoprosthetic device as claimed in claim 1 including a sesamoidal component comprising:
 (i) An elongated flexible planar element including means for securing said element, adjacent a distal end thereof, to said proximal phalanx; and
 (ii) tibial and fibular sesamoidal elements mounted directly onto respective natural sesamoids in spaced lateral relationship to each other adjacent a proximal end thereof, for articulation with said inferior concave sesamoidal surfaces of said metatarsal component.

* * * * *